(12) United States Patent
Radmer

(10) Patent No.: US 12,714,824 B2
(45) Date of Patent: Aug. 25, 2026

(54) INTERMITTENT URINARY CATHETER ASSEMBLY

(71) Applicant: Coloplast A/S, Humlebaek (DK)

(72) Inventor: Bo Radmer, Hilleroed (DK)

(73) Assignee: Coloplast A/S, Humlebaek (DK)

( * ) Notice: Subject to any disclaimer, the term of this patent is extended or adjusted under 35 U.S.C. 154(b) by 825 days.

(21) Appl. No.: 17/921,987

(22) PCT Filed: May 3, 2021

(86) PCT No.: PCT/DK2021/050140

§ 371 (c)(1), (2) Date: Oct. 28, 2022

(87) PCT Pub. No.: WO2021/219188

PCT Pub. Date: Nov. 4, 2021

(65) Prior Publication Data

US 2023/0166073 A1 Jun. 1, 2023

(30) Foreign Application Priority Data

May 1, 2020 (DK) .......................... PA 2020 70276

(51) Int. Cl.
*A61M 25/00* (2006.01)
*A61M 25/01* (2006.01)
*A61M 27/00* (2006.01)

(52) U.S. Cl.
CPC .......... *A61M 25/002* (2013.01); *A61M 25/01* (2013.01); *A61M 27/00* (2013.01);
(Continued)

(58) Field of Classification Search
CPC A61M 25/002; A61M 25/01; A61M 25/0113; A61M 25/0017; A61M 27/002;
(Continued)

(56) References Cited

U.S. PATENT DOCUMENTS 4,062,363 A 12/1977 Bonner, Jr.
5,505,710 A * 4/1996 Dorsey, III ............. A61M 1/84 604/164.11

(Continued)

FOREIGN PATENT DOCUMENTS

EP 2636421 A1 9/2013
SE 505615 C2 * 9/1997 ........ A61M 25/0026

(Continued)

OTHER PUBLICATIONS

English translation of SE-505615-C2 (Year: 1997).*

*Primary Examiner* — Philip R Wiest
(74) *Attorney, Agent, or Firm* — Coloplast Corp., Coloplast A/S; Nick Baumann

(57) ABSTRACT

An intermittent urinary catheter assembly comprising an intermittent urinary catheter comprising a catheter tube (4) with a proximal insertion end (3) and a distal outlet end, the catheter tube comprising a plurality of draining openings (6) at a proximal portion, a handle connected to the distal outlet end of the catheter tube (4), where the handle (30) comprises a first cavity (31) and a coaxial second cavity (33), the first cavity being adapted to provide a through-going hole for draining liquid (urine), and a protective tube (40) adapted for being telescoped in a longitudinal direction between a first proximal position and a second distal position, wherein, in the first proximal position, the protective tube (40) at least partly covers the catheter tube and, in the second distal position, the protective tube is positioned in the second cavity of the handle thereby exposing the full length (L) of the catheter tube for insertion.

12 Claims, 6 Drawing Sheets

(52) U.S. Cl.
CPC ............... *A61M 2025/0175* (2013.01); *A61M 2210/1089* (2013.01)

(58) Field of Classification Search
CPC ... A61M 2025/0175; A61M 2210/1089; A61F 5/455; A61F 5/4556
See application file for complete search history.

(56) References Cited

U.S. PATENT DOCUMENTS 6,544,240 B1* 4/2003 Borodulin ............. A61F 2/0009 604/329
8,728,058 B2* 5/2014 Schertiger ......... A61M 25/0074 604/544
8,827,984 B2* 9/2014 Lovmar ........... A61M 25/0017 604/544
9,233,232 B2 1/2016 Paulen et al.
9,821,142 B2* 11/2017 Hannon .............. A61M 25/001
9,884,167 B2 2/2018 Gustavsson
9,931,486 B2 4/2018 Schertiger et al.
9,937,334 B2 4/2018 Frojd et al.
10,076,636 B2* 9/2018 Murray ............. A61M 25/0017
10,099,032 B2 10/2018 Gustavsson et al.
10,112,031 B2 10/2018 Matthiassen
10,118,019 B2 11/2018 Murray et al.
10,166,366 B2* 1/2019 Murray ............. A61M 25/0017
10,226,594 B1* 3/2019 Palmer .................. A61M 27/00
10,449,328 B2 10/2019 Tanghoej et al.
2003/0004496 A1 1/2003 Tanghoj
2004/0158231 A1* 8/2004 Tanghoj ........... A61M 25/0067 604/544
2005/0004553 A1* 1/2005 Douk ................ A61M 25/0021 604/523
2005/0027236 A1 2/2005 Douk
2006/0025753 A1* 2/2006 Kubalak ............ A61M 25/0111 604/327
2006/0200101 A1 9/2006 Mullejans et al.
2008/0004580 A1 1/2008 Mullejans et al.
2009/0008279 A1 1/2009 Tanghoej
2009/0054876 A1* 2/2009 Borodulin ........... A61M 25/002 604/544
2009/0137985 A1 5/2009 Tanghoej et al.
2009/0318900 A1 12/2009 Tanghoj et al.
2010/0204682 A1* 8/2010 Tanghoj ............ A61M 25/0054 604/544
2010/0211049 A1 8/2010 Schertiger et al.
2010/0211050 A1* 8/2010 Luther .............. A61M 25/0017 604/544
2010/0324540 A1* 12/2010 Paulen ................ A61M 27/008 604/544
2011/0224653 A1 9/2011 Torstensen
2012/0179144 A1* 7/2012 Carleo ............. A61M 25/0017 604/544
2012/0271281 A1 10/2012 Schertiger
2014/0194842 A1 7/2014 Schertiger et al.
2014/0224678 A1 8/2014 Schertiger et al.
2014/0243798 A1* 8/2014 Paulen ................ A61M 25/002 604/544
2014/0262860 A1 9/2014 Hagel
2015/0112313 A1 4/2015 Schertiger
2016/0022959 A1* 1/2016 Schertiger ......... A61M 25/0045 604/544
2016/0038717 A1* 2/2016 Murray ............. A61M 25/0074 604/544
2016/0193447 A1 7/2016 Matthiassen
2017/0173300 A1* 6/2017 Hannon ............ A61M 25/0017
2017/0304590 A1 10/2017 Conway et al.
2018/0036510 A1* 2/2018 Tanghoej .............. A61M 25/01
2018/0126121 A1* 5/2018 Mauch .................. A61M 25/01
2019/0083746 A1 3/2019 Murray et al.
2019/0143078 A1* 5/2019 Tierney .............. A61M 25/0113 604/544
2020/0001043 A1 1/2020 Heneghan et al.
2020/0222659 A1 7/2020 Schertiger et al.
2020/0391005 A1* 12/2020 Murray ............. A61M 25/0017
2021/0100979 A1* 4/2021 Donnelly ........... A61M 25/0111
2022/0134054 A1* 5/2022 Schertiger .......... A61M 25/0113 604/544
2022/0211973 A1* 7/2022 Palmer ................ A61M 27/008
2024/0149016 A1* 5/2024 Eriksson ........... A61M 25/0017

FOREIGN PATENT DOCUMENTS

WO 2014135168 A2 9/2014
WO 2015184365 A1 12/2015
WO 2019123004 A1 6/2019
WO 2019245679 A1 12/2019
WO 2021219188 A1 11/2021

* cited by examiner 100
30
1
28
20
30
20
30
28
40
43
4
6
3
45
2
30
43
3
40
30
43
4
6
3
L 100
3

20
4
40
36
23
29
39
30
33
8
31
43
22
35
4
36
20
40
33
41
30

INTERMITTENT URINARY CATHETER ASSEMBLY

The invention relates to an intermittent urinary catheter assembly.

SUMMARY OF THE INVENTION

Urinary catheter assemblies for draining the bladder are increasingly used for intermittent as well as indwelling or permanent catheterisation. Typically, urinary catheters are used by patients suffering from urinary incontinence or by disabled individuals like paraplegics or tetraplegics, who may have no control permitting voluntary urination and for whom catheterisation may be the way of urinating.

Urinary catheters are divided into two major groups of catheters, indwelling catheters and intermittent catheters. Indwelling catheters are typically inserted into the urethra and the bladder by medical personal (i.e. a trained professional, typically a nurse or physician) and has means for retaining the catheter inside the bladder for up to two weeks or more. Indwelling catheters are soft and flexible since they have to remain in the urethra for weeks. Indwelling catheters empty the bladder continuously.

Intermittent catheters are typically inserted by the user him or herself and sits only in the urethra and bladder for as long as it takes to empty the bladder—e.g. for about 5-10 minutes. Intermittent catheters are used every 4-6 hours to empty the bladder corresponding roughly to the interval that people having no urinary problems will usually go to the bathroom. Intermittent catheters are typically more rigid than indwelling catheters since they have to be inserted by the user him or herself and since they do not need to sit in the urethra for days or weeks. An important feature for the intermittent catheter is to ease the insertion into the urethra. This is done by providing the intermittent catheter with a low frictious surface. Non-limiting examples of such are hydrophilic coated catheters which are subsequently wetted by a swelling media in order to produce a low friction surface, or oil or water-based gel which is applied to the catheter before insertion into the urethra.

Intermittent urinary catheters may be provided with a hydrophilic coating that needs to be wetted prior to use and thereby absorbs a considerable amount of liquid. Such a hydrophilic coating will provide a very lubricious surface that has very low friction when the catheter is to be inserted. Hydrophilic coated catheters, where the coating absorbs a considerable amount of liquid for a low frictious surface (swelling degree>100%), will not be suitable for indwelling catheters, because the hydrophilic surface coating would stick inside the mucosa of the urethra if left inside the body for a longer period, due to the hydrophilic coating transforming from being highly lubricious when fully wetted to being adhesive when the hydration level of the coating is reduced.

This invention relates to intermittent catheters with a hydrophilic coating of the kind that is wetted prior to use to absorb a considerable amount of liquid and to provide a very lubricious surface.

BRIEF DESCRIPTION OF THE DRAWING

The accompanying drawings are included to provide a further understanding of embodiments and are incorporated into and are a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figures 1A, 1B, 1C, 1D, 1E:
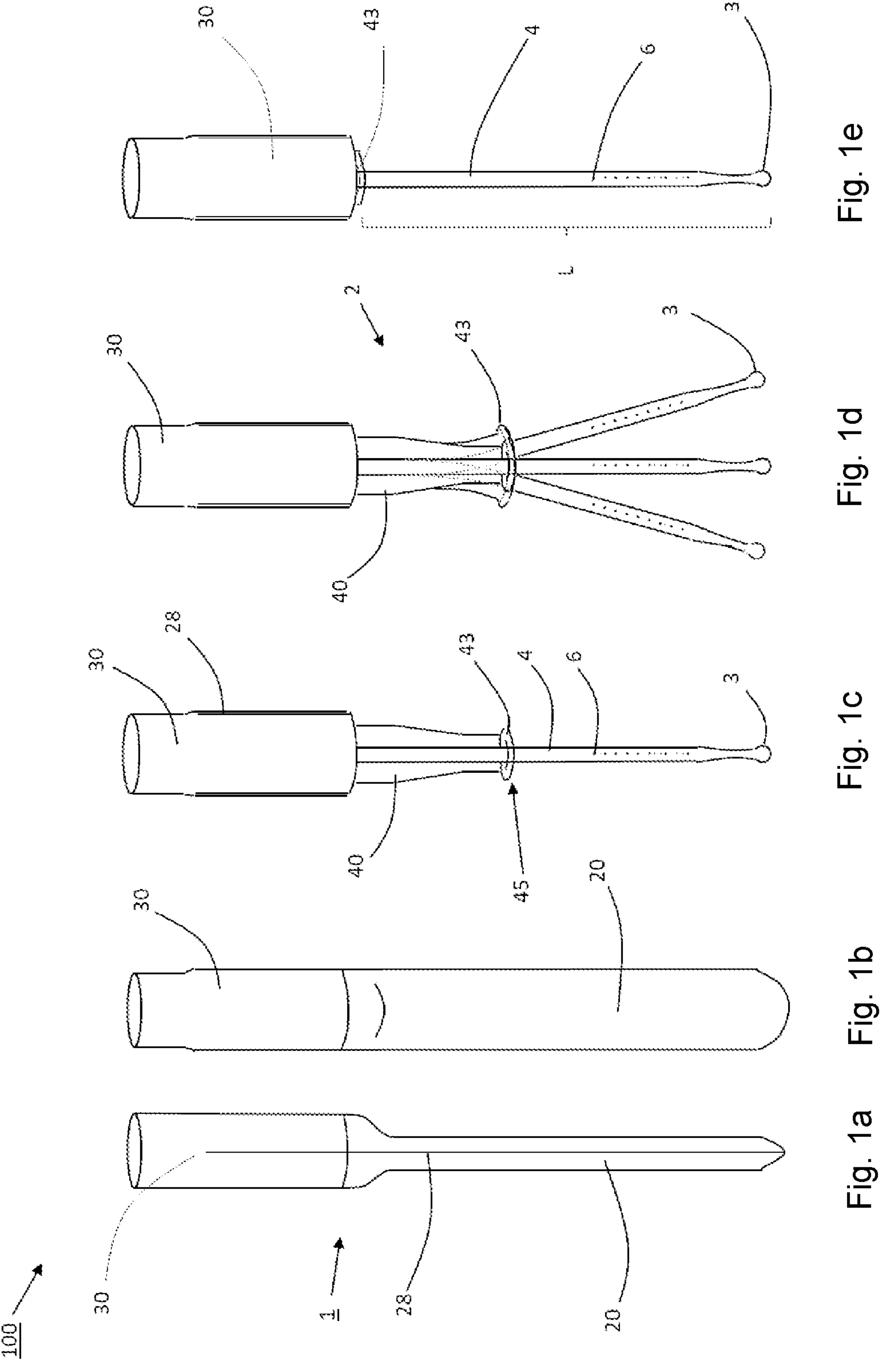
FIG. 1*a*-1*e* illustrate an intermittent urinary catheter assembly in a sequence from storage to use configuration according to the invention.

The invention relates to an intermittent urinary catheter assembly comprising; an intermittent urinary catheter comprising a catheter tube with a proximal insertion end and a distal outlet end, the catheter tube comprising at least two draining openings at a proximal portion, a handle connected to the distal outlet end of the catheter tube, where the handle comprises a first cavity and a second cavity, the first cavity being adapted to provide a through-going hole for draining liquid (e.g. urine), and a protective tube adapted for being telescoped in a longitudinal direction between a first proximal position and a second distal position, wherein, in the first proximal position, the protective tube at least partly covers the catheter tube and, in the second distal position, the protective tube is positioned in the second cavity of the handle thereby exposing the full length of the catheter tube for insertion.

This assembly provides improved handling of the catheter. The assembly provides a longer handle portion towards the proximal end of the catheter tube, allowing the user to move their hands closer to the proximal portion of the catheter. Thereby it is easier for the user to maneuver the catheter insertion end. Additionally, the shortening of a free length of the catheter tube provides an increase of the column strength of the catheter tube. Thereby, the catheter tube is less prone to buckle and collapse during insertion.

Thus, the assembly provides adequate flexibility for navigation, and additionally incorporating column strength to provide adequate stiffness for insertion purpose. Moreover, the protective tube provides a gripper which covers the catheter tube to avoid accidentally touching the catheter tube.

In the following, whenever referring to a proximal end of an element of the invention, the referral is to the end adapted for insertion. Whenever referring to the distal end of an element, the referral is to the end opposite the insertion end.

In other words, the proximal end is the end closest to the user, when the catheter is to be inserted and the distal end is the opposite end—the end furthest away from the user when the catheter is to be inserted. The same definitions apply to the package and container—the proximal end is the end storing the proximal end of the catheter and the distal end is the opposite end.

The longitudinal direction is the direction from the distal to the proximal end. The transverse direction is the direction perpendicular to the longitudinal direction, which corresponds to the direction across the shaft of the catheter.

The catheter described in this application is to be used as an intermittent urinary catheter.

The catheter comprises a catheter tube extending from the distal portion to the proximal portion and constitutes the main portion of the catheter. The tip is positioned in the proximal portion of the catheter and may be provided as a rounded closed end. The tip may also be provided as a spherical or olive shaped bulb in the proximal end with a necked portion distally of the bulb. In this case, the catheter tube extends from the necked portion to the distal portion. The catheter comprises a handle in the distal end, which has a length allowing the user to manipulate the catheter.

Usually, catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus, 8 FR corresponds to a catheter with an outer diameter of 2.7 mm and 18 FR corresponds to a catheter with an outer diameter of 6 mm.

Catheters of this invention may prior to use be provided with a hydrophilic coating so as to impart a low-friction insertion.

The hydrophilic coating may be provided only on the insertable part of the catheter tube. The hydrophilic surface coating is of the kind which, when hydrated or swelled using a swelling medium, reduces the friction on the surface area of the catheter tube which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

The catheter assembly may comprise a container for storage, which may comprise a medium for activating the hydrophilic surface coating of the catheter. The activating medium may be a water-based substance, such as sterile water, saline-solution, or any water-based liquid. Furthermore, the activating medium may be in the form of a vapour contributing material, such as a wetted sponge, woven or non-woven material comprising a vapour contributing liquid. By introducing a vapour contributing material into the container, the vapour will over time hydrate the hydrophilic coating ensuring that the coating is activated and that the hydrophilic coating provides a low-friction surface for the catheter.

In an example, the second cavity is positioned coaxially to the first cavity.

In an example, the catheter tube of the intermittent urinary catheter is non-detachably connected to the handle.

In an example, the protective tube is made from rigid and/or flexible material (e.g. plastic material or silicone material, e.g. ABS, TPE, TPV, PMMA, PE (LD and HD), PP (e.g. PP homo or PP copolymer)), having column strength allowing the protective tube to be moved telescopically in a longitudinal direction between a first proximal position and a second distal position without collapsing. The protective tube may be made of a combination of rigid and flexible material, so that a portion of the tube closest to the handle is more rigid than a portion of the tube furthest away from the handle. In an example, the protective tube may be manufactured by a two-component injection moulding. Due to the telescopic movement, the resistance provided by the protective tube against insertion is minimized.

The protective tube provides a soft pliable extended handle that allows flexibility of the protective tube and the catheter tube but still provides column strength allowing telescopic movement of the protective tube into the handle with a minimum of resistance.

In an example, the handle comprises a flange stop adapted to stop telescopic movement of the protective tube further than the first proximal position. Hereby the protective tube is prevented from telescope further than the first proximal position, towards the proximal insertion end.

In an example, the assembly comprises a container adapted for enclosing the catheter tube of the intermittent urinary catheter and the protective tube during storage.

In another example, the assembly comprises a pouch adapted for enclosing the catheter tube of the intermittent urinary catheter and the protective tube during storage.

In an example, the container and the handle comprise complementary shaped snap-fit elements. Alternatively, the handle and the container may comprise complementary bayonet interface or screw thread adapted for coupling and decoupling.

In an example, the protective tube comprises a tip protrusion at the proximal end.

In an example, the container comprises an inwardly protruding flange adapted to provide a detachable snap fit cooperating with the tip protrusion of the protective tube.

In an example, the protective tube and the container comprises complementary shaped releasable snap fit connections adapted to telescope the protective tube out of the inner lumen of the handle as the container is removed from the handle.

Alternatively, couplings and connections could be by snap fit, welding, gluing or they could be joint by an interference fit, also known as a press fit or friction fit.

In an example, the complementary shaped releasable snap fit connections are friction fit coupling means. In another embodiment, the complementary shaped releasable snap fit connections are a gripper and a protrusion.

In an example, the catheter tube comprises an exposed length of 95 mm, such as 94, 93, 92, 91, 90 mm or even 85 mm; such as 96, 97, 98, 100 mm or longer, when the protective tube is in the second distal position.

In an example, the protective tube comprises one or more protective tube parts, the one or more protective tube parts being telescopically movable with respect to each other in the longitudinal direction of the catheter assembly. Due to the telescopic movement, the resistance against insertion provided by the protective tube is minimized.

Another aspect relates to a method of using an intermittent urinary catheter assembly, where the method comprises the steps of; providing a catheter assembly including an intermittent urinary catheter having a catheter tube with a proximal insertion end and a distal outlet end; a handle connected to the catheter tube at the distal outlet end and a protective tube, providing the protective tube in the first proximal position such that the protective tube covers a part of the catheter tube to be inserted, inserting the catheter tube into the urethra, while holding the handle and optionally also the protective tube, letting go of the protective tube during insertion so as to allow it to telescope into the handle.

In an example, the method is initiated by the step of removing the container and simultaneously pulling the protective tube to the first proximal position to cover at least partly the catheter tube.

Generally, the protective tube may be arranged in the first position, either during manufacturing or the protective tube may be arranged in the first position by the user either by removing the container or manually after the container has been removed.

DETAILED DESCRIPTION OF THE DRAWING

Initially, it shall be noted that the figures are schematic illustrations intended only to address the principles and functions of the catheter assembly according to the invention and are not to be considered limiting to the scope of the attached claims. Furthermore, the figures and particularly the individually illustrated elements are not necessarily to scale, neither individually nor in relation to each other.

Embodiments, and features of the various exemplary embodiments described in this application, may be combined with each other ("mixed and matched"), unless specifically noted otherwise.

FIG. 1 illustrates an intermittent urinary catheter assembly 100. The catheter assembly is illustrated in five different side views a-e in sequence from a storage configuration to a use configuration.

The assembly 100 comprises a package 1 with a container 20 and a handle 30.

Side views 1*a* and 1*b* illustrate the assembly in storage configuration, the container 20 being connected to the handle 30. The package 1 comprises a ridge 28 in the longitudinal direction which may provide better grip for a user and/or may provide visible guide for how to reconnect the container to the handle. The two side views are rotated 90 degrees with respect to each other.

In side views 1*c* and 1*d* the catheter 2 is illustrated. The catheter 2 has a catheter tube 4 having a proximal insertion end 3. A proximal portion of the catheter tube 4 is provided with a plurality of draining openings 6 functioning as inlets for the liquid (urine). The assembly further comprises a flexible protective tube 40 adapted to partly cover the catheter tube 4 before use of the catheter. The protective tube comprises a tube-shape encircling coaxial the catheter tube 4.

The flexible protective tube 40 telescope into the handle as the catheter tube is inserted into the urethra for exposing the full insertable length of the catheter tube 4 to be inserted. Side view 1*e* illustrates the catheter 2 having the full insertion length L of the catheter tube 4 exposed. The flexible protective tube 40 is telescoped inside the handle 30, and only the proximal tip protrusion 43 of the protective tube 40 is visible.

FIG. 1 illustrates the protective tube 40 telescoped between a first proximal position and a second distal position. Side views 1*c* and 1*d* illustrate the protective tube in the first proximal position and side view 1*e* of FIG. 1 illustrates the protective tube in the second distal position.

In the first proximal position the protective tube 40 partly covers the catheter tube 4, and in the second distal position the protective tube 40 is telescopically slid into a cavity of the handle 30. In other words, in the first proximal position the protective tube 40 partly covers the catheter tube 4, and a user may use the protective tube 40 as an extended handle. In the second distal position the catheter tube 4 is fully exposed and the protective tube 40 is positioned inside the second cavity of the handle 30.

The protective tube 40 provides a soft extended handle, that may be made of a material, such as silicone, that is soft to allow flexibility of the protective tube and the catheter tube 4, but still provides column strength allowing telescopic movement of the protective tube 40 into the handle with a minimum of resistance.

The length (L) of the fully exposed catheter tube 4, when the protective tube is in the second distal position, may be 95 mm, such as about 60, 70, 75, 80, 90, 100 or 110 mm; such as 50-120, 60-110, 70-100 mm.

In the storage configuration, the protective tube is positioned in the second distal position and withdrawn from the handle to the first proximal position prior to use. After use, the protective tube is repositioned in the second distal position and the narrow container 20 can be reconnected to the handle 30 before disposal.

Figures 2, 3:
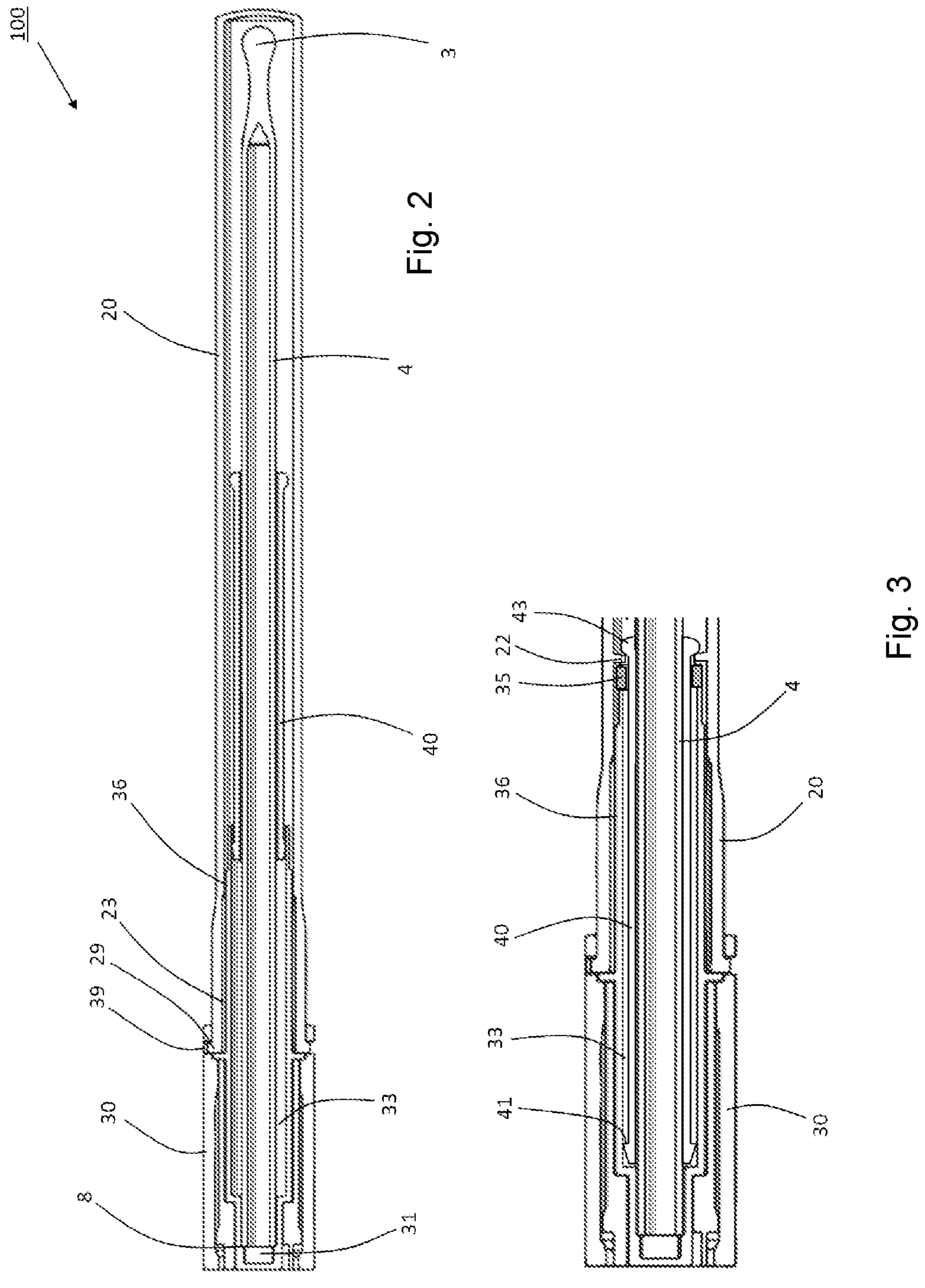
FIG. 2 illustrates an embodiment of an intermittent urinary catheter assembly in a side view.
FIG. 3 illustrates an enlarged schematic sideview of the handle portion of the intermittent urinary catheter illustrated in FIG. 2.

FIG. 2 illustrates another embodiment of an intermittent urinary catheter assembly 100 in a side view. The protective tube 40 is in the first proximal position coaxially encircling the catheter tube 4. The distal outlet end 8 of the catheter tube is fixed to the handle 30 at a first cavity 31. The container 20 is snap-locked to the handle 30 at the distal end of the container by an outwardly extending flange 29 on the container and a groove 39 in the handle. The handle comprises a second cavity 33 adapted for accommodating the protective tube 40. The second cavity 33 is arranged coaxially to the first cavity 31.

The handle furthermore comprises a proximal handle portion 36 and a clearance 23 on the outer surface of the proximal handle portion 36 allowing the container 20 to be moved inward releasing the outwardly extending flange 29 from the groove 39 of the handle. Thereby, the container 20 can be removed from the assembly.

FIG. 2 and FIG. 3 illustrates the intermittent urinary catheter assembly in a storage configuration having the container 20 connected to the handle 30. In FIG. 2, the protective tube 40 is arranged in the first proximal position, and in FIG. 3, the protective tube is arranged inside the second cavity 33, only the proximal tip protrusion 43 is arranged outside the handle, such that a snap fit element 22 of the protective tube 40 can engage with the tip protrusion 43. The container is snap-locked to the handle. The protective tube 40 and the container 20 comprise complementary shaped releasable snap fit connections 22,41. As the container is removed from the handle to expose the catheter tube, the protective tube 40 is telescoped from the second distal position inside the handle to the first proximal position before the container disengage with the tip of the protective tube 40.

FIG. 3 schematically shows the handle provided with a flange stop 35 for an outwardly extending flange 41 of the protective tube 40. The flange stop 35 is adapted to stop movement of the protective tube towards the proximal insertion end 3.

Figure 4:
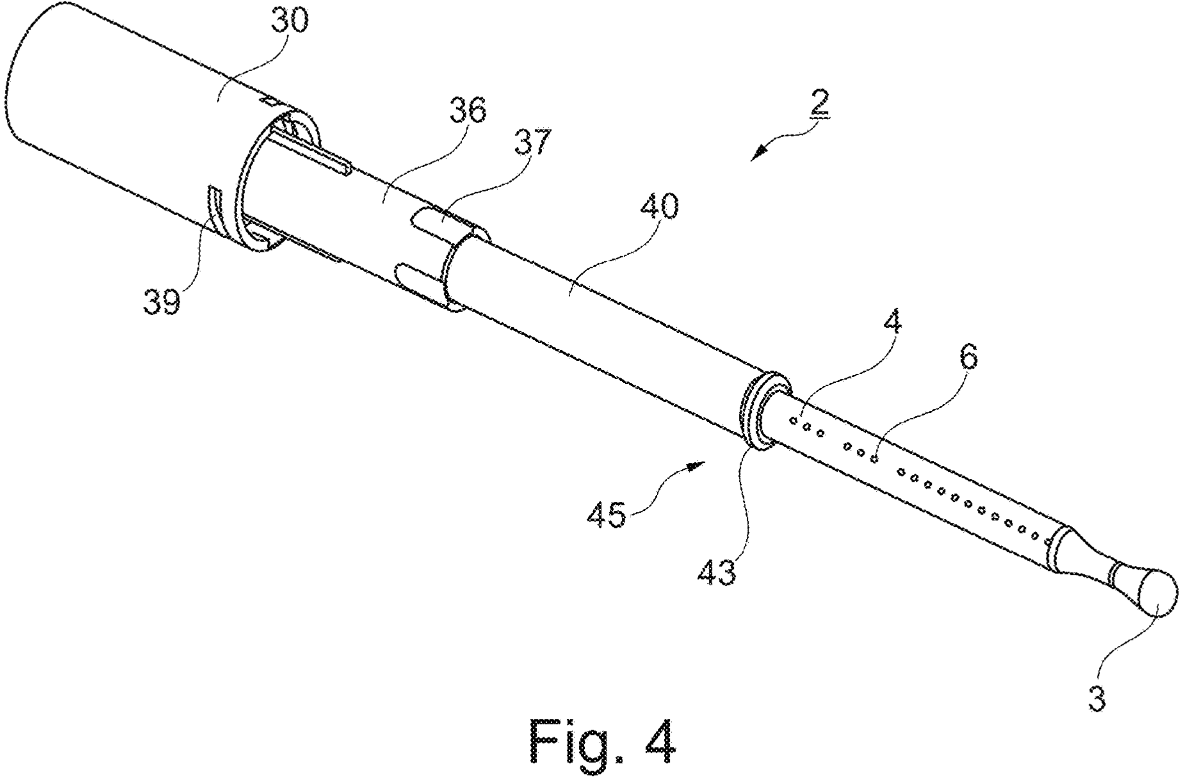
FIG. 4 illustrates the intermittent urinary catheter illustrated in FIG. 2 in a perspective view in a use-configuration.

FIG. 4 illustrates the intermittent urinary catheter 2 in a use-configuration having the protective tube 40 in the first proximal position. The proximal portion of the catheter tube 4 has a plurality of draining openings is exposed.

The handle 30 comprises a proximal extending handle portion 36 having a recess 37 exposing the proximal tip portion 43. The proximal handle portion has a smaller diameter in a radial direction than the handle as to provide an inner guide for the container when the package is re-closed. The protective tube 40 comprises a narrow end portion 46. For providing better stability during insertion. A smaller clearance between the catheter tube and the protective tube provides for less buckling of the catheter tube—and thereby better stability during insertion.

Figure 5:
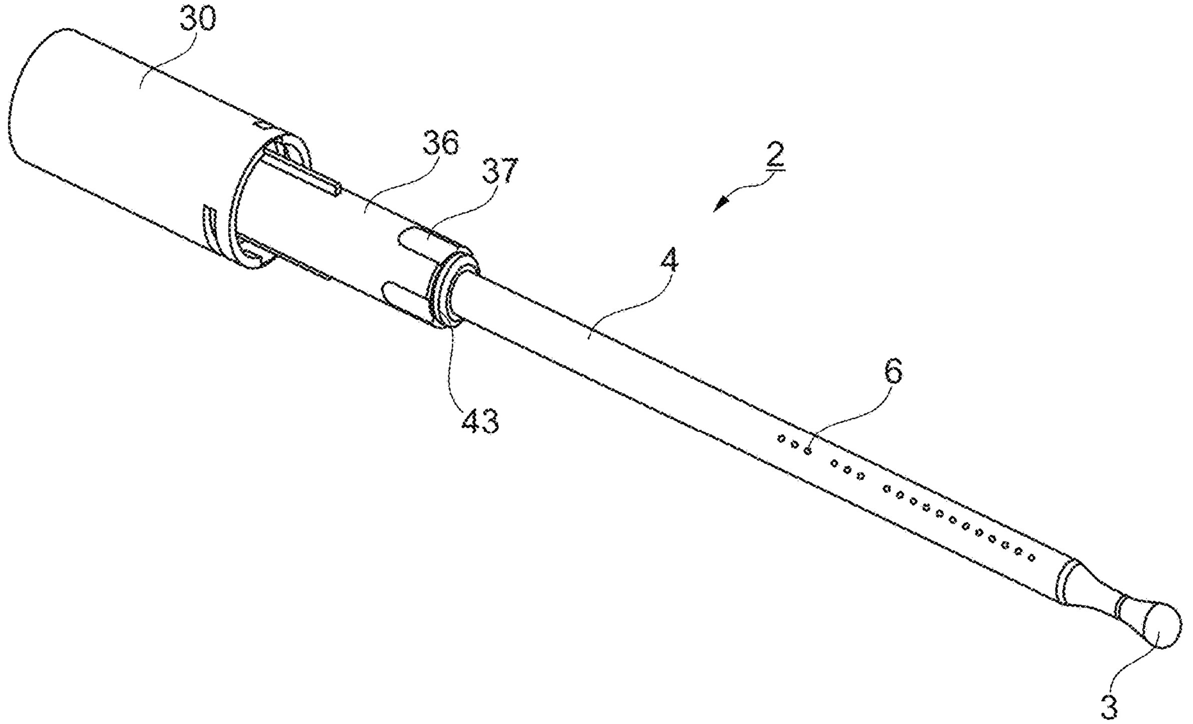
FIG. 5 illustrates the intermittent urinary catheter as illustrated in FIGS. 2, 3 and 4 comprising a protective tube in a second distal position.

FIG. 5 illustrates the intermittent urinary catheter 2 in a use-configuration having the protective tube in the second distal position, and the insertable length of the catheter tube is fully exposed.

Figure 6:
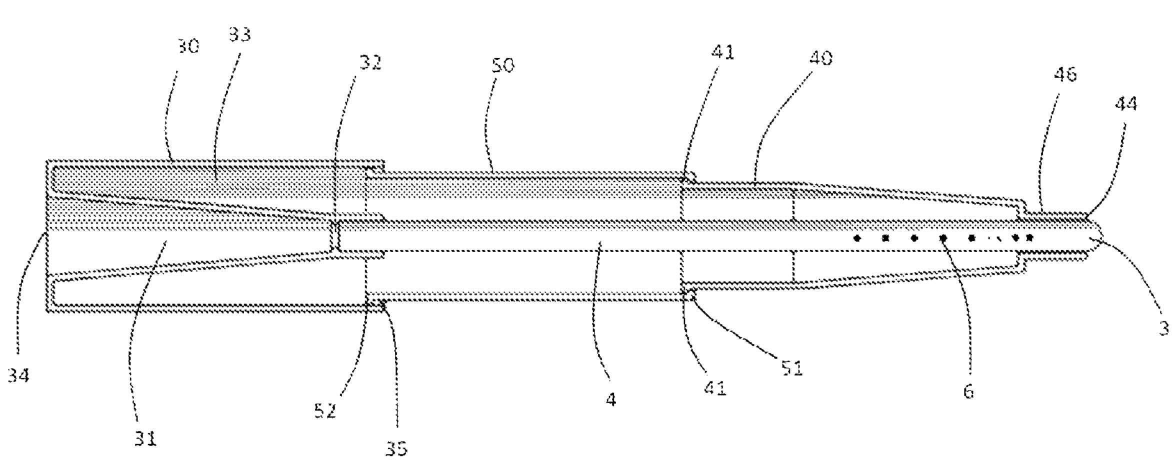
FIG. 6 illustrates a side view of another embodiment of an intermittent urinary catheter comprising telescopic protective tubes.

FIG. 6 illustrates a side view of another embodiment of an intermittent urinary catheter comprising telescopic protective tubes 40,50. Each of the protective tubes comprises a tube-shape and being positioned coaxial encircling the catheter tube 4.

The catheter tube 4 extends in the longitudinal direction from the proximal insertion end 3 to a distal end forming a connection 32 to the handle 30, such that liquid (urine) can be drained via the plurality of draining openings 6 through the catheter tube 4 and the first cavity 31 to a distal outlet 34 at the handle distal end.

The handle 30 is provided with a second cavity 33 and an inwardly extending flange 35 functioning as a stop for the protective tubes at the proximal end of the handle. The protective tube 40 comprises a protective tube part 50. The protective tube may be made of rigid plastic material. The protective tube 40 and the protective tube part 50 adapted to telescopically slide in the longitudinal direction into each other and into the second cavity 33 of the handle 30, see also FIG. 9.

The protective tube 40 comprises, at the truncated proximal portion, a narrow end portion 46 provide with an end opening 44 slightly larger than the diameter of the catheter tube 4. At the distal end, the protective tube is provided with an outwardly extending flange 41 functioning as a stop against an inwardly protruding flange 51 of a protective tube part 50. The protective tube part 50 comprises a radially outward extending flange functioning as a stop toward the inwardly extending flange 35 of the handle.

Figure 7:
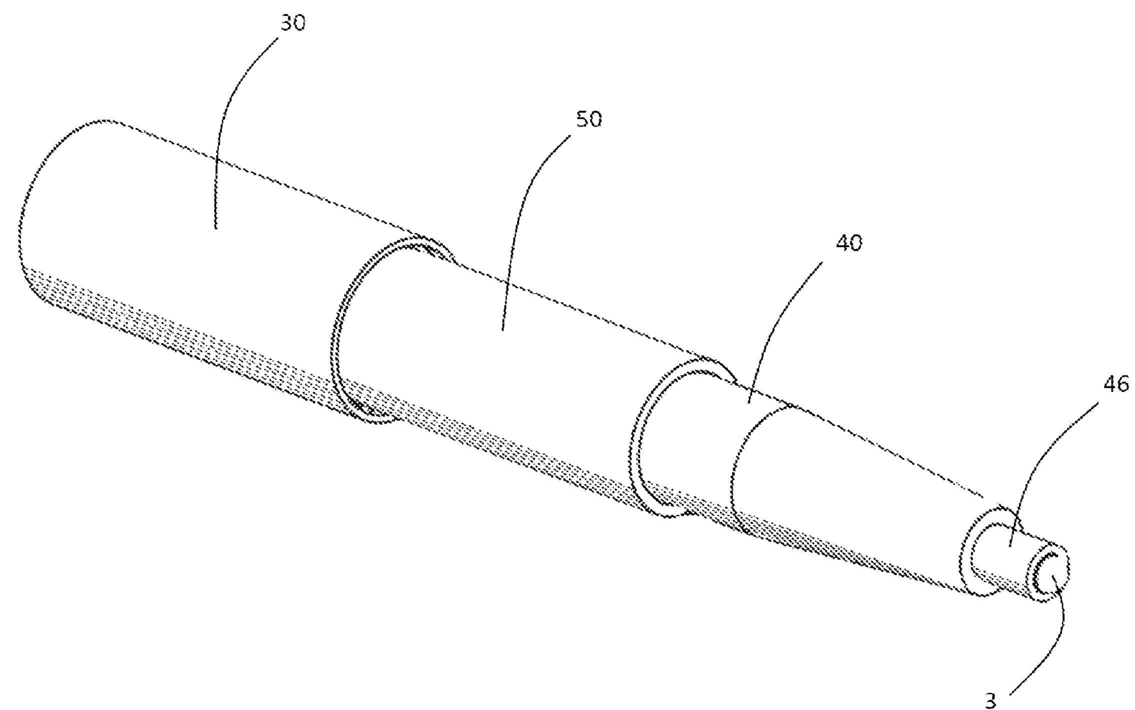
FIG. 7 illustrates the catheter illustrated in FIG. 5 in a perspective view.

FIG. 7 shows the catheter illustrated in FIG. 6 in a perspective view.

Figures 8, 9:
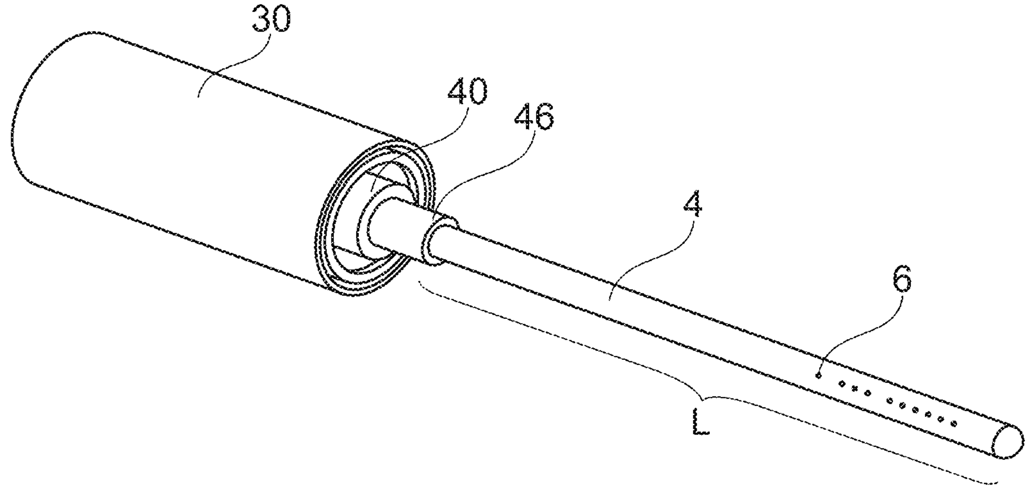
FIG. 8 illustrates in a perspective view the catheter as illustrated in FIGS. 4 and 5, the catheter tube is fully exposed
FIG. 9 illustrates in a side view a handle and a protective tube.

FIG. 8 illustrates in a perspective view the catheter as illustrated in FIGS. 6 and 7, the protective tube is telescopically slid into the handle and the catheter tube for insertion is fully exposed.

FIG. 9 illustrates a side view of the catheter assembly.

The handle 30 comprises a first and a second cavity 31,33, the second cavity 33 being arranged coaxially to the first cavity 31. The protective tube 40 is telescoped into the second cavity 33 to a second position to fully expose the catheter tube 4. The protective tube 40 comprises two protective tube parts 50,60. The protective tube and protective tube parts may be made of rigid plastic material. The protective tube 40 and the two protective tube parts 50,60 are telescopically slid in longitudinal into each other and into the second cavity 33 of the handle 30.

Generally, the second cavity may comprise a cylinder-shaped cavity encircling coaxially to the circular cylinder shaped first cavity.

The invention claimed is:

1. An intermittent urinary catheter assembly comprising:

an intermittent urinary catheter comprising a catheter tube with a proximal insertion end and an insertion portion extending from the proximal insertion end toward a distal outlet end, the catheter tube comprising a lubricious coating and a plurality of drain openings formed in a longitudinal direction along a proximal portion of the catheter tube, a handle coupled with the distal outlet end of the catheter tube, the handle comprising a first cavity and a second cavity, the first cavity forms a through-going hole to allow liquid entering the plurality of drain openings of the catheter tube to exit a distal end of the handle, a protective tube telescopically disposed in the second cavity of the handle, and a container attachable to the handle and adapted for enclosing the catheter tube of the intermittent urinary catheter and the protective tube during storage of the intermittent urinary catheter assembly, wherein the protective tube is adapted to telescope out of the second cavity of the handle to cover and protect at least a portion of the insertion portion of the catheter tube, wherein the protective tube is adapted to retract into the second cavity of the handle to fully expose an entire length of the insertion portion of the catheter tube for insertion into a urethra, wherein the protective tube comprises a tip protrusion at the proximal end and the tip protrusion is sized to prevent the proximal end of the protective tube from entering into the handle, wherein the container comprises an inwardly protruding flange adapted to provide a detachable snap-fit that cooperates with and couples the container to the tip protrusion of the protective tube.

2. The intermittent urinary catheter assembly according to claim 1, wherein the second cavity is positioned coaxial to the first cavity.

3. The intermittent urinary catheter assembly according to claim 1, wherein the catheter tube of the intermittent urinary catheter is fixedly connected to the handle.

4. The intermittent urinary catheter assembly according to claim 1, wherein the handle comprises a flange stop adapted to prevent the protective tube from detaching from the handle.

5. The intermittent urinary catheter assembly according to claim 1, wherein the container and the handle comprise complementary shaped snap-fit elements.

6. The intermittent urinary catheter assembly according to claim 1, wherein the protective tube and the container each comprises complementary shaped releasable snap-fit connections adapted to telescope the protective tube out of the second cavity of the handle as the container is removed from the handle.

7. The intermittent urinary catheter assembly according to claim 1, wherein the complementary shaped releasable snap-fit connections are friction fit one to another.

8. The intermittent urinary catheter assembly according to claim 1, wherein the protective tube comprises two protective tube parts, the two protective tube parts being telescopically movable with respect to each other in a longitudinal direction of the catheter assembly.

9. An intermittent urinary catheter assembly comprising:

an intermittent urinary catheter comprising a catheter tube with a proximal insertion end and an insertion portion extending from the proximal insertion end toward a distal outlet end, the catheter tube comprising a lubricious coating and a plurality of drain openings formed in a longitudinal direction along a proximal portion of the catheter tube, a handle coupled with the distal outlet end of the catheter tube, the handle comprising a first cavity and a second cavity, the first cavity forms a through-going hole to allow liquid entering the plurality of drain openings of the catheter tube to exit a distal end of the handle, a protective tube telescopically disposed in the second cavity of the handle, and a container attachable to the handle and adapted for enclosing the catheter tube of the intermittent urinary catheter and the protective tube during storage of the intermittent urinary catheter assembly, wherein the protective tube is adapted to telescope out of the second cavity of the handle to cover and protect at least a portion of the insertion portion of the catheter tube, wherein the protective tube is adapted to retract into the second cavity of the handle to fully expose an entire length of the insertion portion of the catheter tube for insertion into a urethra, wherein the protective tube and the container each comprises complementary shaped releasable snap-fit connections adapted to telescope the protective tube out of the second cavity of the handle as the container is removed from the handle.

10. An intermittent urinary catheter assembly comprising:

an intermittent urinary catheter comprising a catheter tube with a proximal insertion end and an insertion portion extending from the proximal insertion end toward a distal outlet end, the catheter tube comprising a lubricious coating and a plurality of drain openings formed in a longitudinal direction along a proximal portion of the catheter tube, a handle coupled with the distal outlet end of the catheter tube, the handle comprising a first cavity and a second cavity, the first cavity forms a through-going hole to allow liquid entering the plurality of drain openings of the catheter tube to exit a distal end of the handle, a protective tube telescopically disposed in the second cavity of the handle, and a container attachable to the handle and adapted for enclosing the catheter tube of the intermittent urinary catheter and the protective tube during storage of the intermittent urinary catheter assembly, wherein the protective tube is adapted to telescope out of the second cavity of the handle to cover and protect at least a portion of the insertion portion of the catheter tube, wherein the protective tube is adapted to retract into the second cavity of the handle to fully expose an entire length of the insertion portion of the catheter tube for insertion into a urethra, wherein the protective tube and the container each comprises complementary shaped releasable snap-fit connections adapted to telescope the protective tube out of the second cavity of the handle as the container is removed from the handle, wherein the complementary shaped releasable snap-fit connections are friction fit one to another.

11. A urinary catheter assembly comprising:

an intermittent urinary catheter comprising a catheter tube with a proximal insertion end and an insertion portion extending from the proximal insertion end, the catheter tube comprising a plurality of drain openings formed in a longitudinal direction along a proximal portion of the catheter tube as a linear array of more than five drainage openings, a handle coupled with the distal outlet end of the catheter tube, the handle comprising a through-going hole to allow liquid entering the plurality of drain openings of the catheter tube to exit a distal end of the handle, a protective tube telescopically disposed in the handle, and a container attachable to the handle and adapted for enclosing the catheter tube of the intermittent urinary catheter and the protective tube during storage of the intermittent urinary catheter assembly, wherein the protective tube is adapted to telescope out of the handle to fully expose an entire length of the insertion portion of the catheter tube for insertion into a urethra, wherein the protective tube and the container each comprises complementary shaped releasable snap-fit connections adapted to telescope the protective tube out of the handle as the container is detached from the handle.

12. The urinary catheter assembly according to claim 11, wherein the protective tube comprises a tip protrusion at the proximal end and the container comprises an inwardly protruding flange adapted to provide a detachable snap-fit that cooperates with and couples the container to the tip protrusion of the protective tube.

* * * * *